US010353222B2

(12) United States Patent
Le

(10) Patent No.: US 10,353,222 B2
(45) Date of Patent: Jul. 16, 2019

(54) METHODS FOR MEASURING ACTUAL DISTANCE OF HUMAN BODY AND CUSTOMIZING SPECTACLE FRAME

(71) Applicant: I-GLASSES VISION TECHNOLOGY LLC, Guangzhou (CN)

(72) Inventor: Meihua Le, Guangzhou (CN)

(73) Assignee: I-GLASSES VISION TECHNOLOGY LLC, Guangzhou (CN)

( * ) Notice: Subject to any disclaimer, the term of this patent is extended or adjusted under 35 U.S.C. 154(b) by 38 days.

(21) Appl. No.: 15/735,223

(22) PCT Filed: May 5, 2016

(86) PCT No.: PCT/CN2016/081194
§ 371 (c)(1),
(2) Date: Dec. 11, 2017

(87) PCT Pub. No.: WO2017/173694
PCT Pub. Date: Oct. 12, 2017

(65) Prior Publication Data

US 2018/0180905 A1 Jun. 28, 2018

(30) Foreign Application Priority Data

Apr. 6, 2016 (CN) .......................... 2016 1 0209496

(51) Int. Cl.
*G02C 13/00* (2006.01)
*A61B 3/11* (2006.01)
(Continued)

(52) U.S. Cl.
CPC ............ *G02C 13/003* (2013.01); *A61B 3/111* (2013.01); *A61B 5/107* (2013.01); *G02C 13/005* (2013.01);
(Continued)

(58) Field of Classification Search
CPC ...... G02C 13/003; G02C 13/005; G06T 7/60; G06T 17/00; G06T 2207/30201;
(Continued)

(56) References Cited

U.S. PATENT DOCUMENTS

| | | | | |
|---|---|---|---|---|
| 6,533,418 | B1 | 3/2003 | Izumitani et al. | |
| 2006/0291702 | A1 * | 12/2006 | Miessbacher ...... | G06K 9/00604 382/117 |
| 2015/0049952 | A1 * | 2/2015 | Cholayil ................ | A61B 5/107 382/195 |

FOREIGN PATENT DOCUMENTS

| | | | |
|---|---|---|---|
| CN | 1264474 | A | 8/2000 |
| CN | 101059871 | A | 10/2007 |

(Continued)

OTHER PUBLICATIONS

Liu Yudong, "The research on glass online customization system design based on three-dimension of head and its experience", Dissertation for master degree.

(Continued)

*Primary Examiner* — Tapas Mazumder
(74) *Attorney, Agent, or Firm* — Gokalp Bayramoglu

(57) ABSTRACT

A method for measuring the actual distance of a human body based on a cornea image and a method for customizing a spectacle frame. The measurement method comprises the following steps: step 1, acquiring a front-view photograph with at least one dark part of eyes, or capturing a frame of a front-view image with at least one dark part of eyes from a video; step 2, detecting and positioning the first dark part; step 3, determining a max horizontal radius $L_p$ of the first dark part; step 4, determining a proportionality factor η of an actual linear geometric size to a linear size in the photograph or the frame; and step 5, measuring an actual image distance between any two points, and multiplying the actual image distance by the proportionality factor η to
(Continued)

Acquiring an image with dark parts of eyes
↓
Detecting and positioning a dark part
↓
Determining a max horizontal radius of the dark part
↓
Determining a proportionality factor of an actual linear geometric size to a linear size in the image
↓
Calculating an actual distance between any two points on the human body obtain an actual distance between the two corresponding points on human body.

9 Claims, 2 Drawing Sheets

(51) Int. Cl.

| | |
|---|---|
| ***G06K 9/00*** | (2006.01) |
| ***G06T 17/00*** | (2006.01) |
| ***A61B 5/107*** | (2006.01) |
| ***G06T 7/60*** | (2017.01) |

(52) U.S. Cl.

CPC ................ *G06T 7/60* (2013.01); *G06T 17/00* (2013.01); *G06K 9/00604* (2013.01); *G06T 2207/10016* (2013.01); *G06T 2207/30201* (2013.01)

(58) Field of Classification Search

CPC ........... G06T 2207/10016; A61B 3/111; A61B 5/107; G06K 9/00604

See application file for complete search history.

(56) References Cited

FOREIGN PATENT DOCUMENTS

| | | |
|---|---|---|
| CN | 102278978 A | 12/2011 |
| CN | 104808797 A | 7/2015 |

OTHER PUBLICATIONS

David Balya,"Face and Eye Detection by CNN Algorithms",Journal of VLSI Signal Processing 23, p. 497-511 (1999).

Antonio Haro,"Detecting and tracking eyes by using their physiological properties, dynamics, and appearance", Proc. of IEEE International Conference on Computer Vision and Pattern Recognition, 2000, vol. 1, p. 163-168.

So-Hee Park,"A new implementation method of ASEF for eye detection", 7th International Conference on Computing and Convergence Technology (ICCTT), p. 1034-1037.

* cited by examiner

METHODS FOR MEASURING ACTUAL DISTANCE OF HUMAN BODY AND CUSTOMIZING SPECTACLE FRAME

CROSS REFERENCE TO RELATED APPLICATIONS

This application is the national phase entry of International Application No. PCT/CN2016/081194, filed on May 5, 2016, which is based upon and claims priority to Chinese Patent Application No. CN2016102094962, filed on Apr. 6, 2016, the entire contents of which are incorporated herein by reference.

TECHNICAL FIELD

The invention relates to the technical field of distance measurement, and particularly to a method for measuring an actual distance of human body based on the cornea, and customizing a spectacle frame based on the method for measuring the actual distance of human body.

BACKGROUND

It is necessary to actually measure a distance between two corresponding points on a human body when customizing products such as clothes and spectacles. Spectacles mainly consist of lenses and spectacle frames. It is also necessary to customize a spectacle frame due to the differences in the facial structures, such as the pupil distance, the height and width of the nose bridge, and the distance from the corneal apex to the top plane of an ear. Conventional spectacle frames are mass-produced in factories based on common parameters and thus it is not suitable for customization. In order to customize a spectacle frame, people have to go to an eyeglass store or an optometry center for parameter determination and manual adjustment based on their own feelings, which take a lot of time. Moreover, manual measurements will sometime bring in parameter errors, making the spectacles with the customized frame uncomfortable. Therefore, it is very necessary for a customer to fabricate a spectacle frame matching anatomical data of his/her own head and face based on parameters such as the anatomical shape of the nose bridge and the distance from the corneal apex to the top plane of an ear. In this way, the stability of the spectacle frame during wearing is enhanced to improve the experiences of the lens such as children's myopia control lenses and progressive lenses; moreover, the efficiency of prescribing spectacles and the wearing comfortability of the spectacles are greatly improved.

SUMMARY

In view of the above deficiencies, an objective of the present invention is to provide a method for measuring an actual distance between any two points on a human body based on an image of the cornea, which enables measuring the body parameters off-site. Through the actually measurement on a cornea (the dark part of an eye, in practice), the actual distance between any two points on a human body can be determined based on a max horizontal radius obtained from an image of the cornea, which facilitates the customization.

To achieve the above objective, the following technical solutions are adopted.

Provided is a method for measuring an actual distance of human body based on an image of cornea, the method comprising the following steps:

step 1, acquiring a front-view photograph with one or both dark parts of eyes in it, or capturing a frame of front-view image with one or both dark parts of eyes in it from a video;

step 2, detecting and positioning one of the dark parts in the front-view photograph or the frame of front-view image;

step 3, determining a max horizontal radius $L_p$ of the one of the dark parts;

step 4, determining a proportionality factor $\eta$ of an actual linear geometric size to a linear size in the photograph or the frame based on the max horizontal radius $L_p$; and step 5, measuring an actual image distance between any two points in the front-view photograph or the frame of front-view image, and multiplying the actual image distance by the proportionality factor $\eta$ to obtain an actual distance between the two corresponding points on human body.

Said step 3 comprises the following steps:

step 31, placing the one of the dark parts in a first quadrant of an X-Y coordinate system;

step 32, selecting the one of the dark parts, and obtaining a set I (x,y) of positive integers x and y in a image I of the selected dark part, wherein $0 \le x \le x_1$, $0 \le y \le y_1$, and $x_1$ and $y_1$ are respectively a maximum horizontal coordinate and a maximum vertical coordinate in the image of the dark part;

step 33, capturing a subimage $I_1$ from the image I of the dark part for eliminating interferences of upper and lower eyelids in the image of the dark part, the subimage $I_1$ satisfying $I_1 = I_1(x', y')$, for $0 \le x' \le x_1$ and $y_1/4 \le y' \le 3y_1/4$; and step 34, acquiring all positive integers INT (y') satisfying $y_1/4 \le y' \le 3y_1/4$, determining a maximum value of x' and a minimum value of x' corresponding to each of the positive integers INT (y'), subtracting the minimum value of x' from the maximum value of x' to obtain a maximum difference value of x' corresponding to each of the positive integers INT (y'), and taking a maximum value in the maximum difference values of x' corresponding to all of the positive integers INT (y') as the max horizontal radius $L_p$ being expressed as:

$$L_p = \max_{i=1}^{n} [x_{max}(\mathrm{INT}_i(y')) - x_{min}(\mathrm{INT}_i(y'))],$$

wherein $x_{max}(\mathrm{INT}_i(y'))$ and $x_{min}(\mathrm{INT}_i(y'))$ are respectively the maximum value of x' and the minimum value of x' corresponding to the i-th positive integer INT(y'); n is the number of the positive integers INT (y') satisfying $y_1/4 \le y' \le 3y_1/4$, and $1 \le i \le n$.

The method for determining the proportionality factor $\eta$ in the step 4 is as follows:

$$\eta = \frac{L_r}{L_p},$$

wherein, $L_r$ is an actually measured value of a max horizontal radius of an actual dark part of eye on human body corresponding to the one of the dark parts.

Another objective of the present invention is to apply the above method for measuring the body parameters off-site in the customization of spectacle frames. The method allows a person to immediately design spectacle frames by himself/herself or directly send front-view images and side-view images of human face to an eyeglass store or an optometry center for frames design, which saves a lot of time and provides accurate data, and thus the spectacle frames fit the person and are comfortable.

Provided is a method for customizing a spectacle frame, the method comprising the following steps:

step 10, taking photographs or taking a video of a human face of a person by a mobile device or a computer; acquiring a front-view image and a side-view image from the photographs, or acquiring a frame of front-view image and another frame of side-view image from the video;

step 20, detecting and positioning an eye in the front-view image;

step 30, determining a max horizontal radius $L_p$ of a dark part of the eye in the front-view image;

step 40, determining a proportionality factor η of an actual linear geometric size to a linear size in the front-view image based on the max horizontal radius $L_p$;

step 50, measuring a pupil distance $L_1$, a width $L_2$ of a nose bridge and a height H of the nose bridge in the front-view image, measuring a distance $L_3$ from a cornea apex to a top of an ear in the side-view image, and multiplying the pupil distance $L_1$, the width $L_2$ of the nose bridge, the distance $L_3$ from the cornea apex to the top of the ear and the height H of the nose bridge respectively by the proportionality factor η to obtain an actual pupil distance $L_1'$, an actual width $L_2'$ of the nose bridge, an actual distance $L_3'$ from the cornea apex to the top of the ear and an actual height H' of the nose bridge of the person; and step 60, transmitting the actual pupil distance $L_1'$, the actual width $L_2'$ of the nose bridge, the actual distance $L_3'$ from the cornea apex to the top of the ear and the actual height H' of the nose bridge of the person to the mobile device or the computer to perform a 3D modeling, and transmitting results of the 3D modeling to a data center or a 3D printer.

Said step 30 comprises the following steps:

step 301, placing the front-view image in a first quadrant of an X-Y coordinate system;

step 302, selecting a image I of the eye in the front-view image, and obtaining a set I (x,y) of positive integers x and y in the image I of the eye, wherein $0 \le x \le x_1$, $0 \le y \le y_1$, and $x_1$ and $y_1$ are respectively a maximum horizontal coordinate and a maximum vertical coordinate in the front-view image;

step 303, capturing a subimage $I_1$ from the image I of eye for eliminating interferences of upper and lower eyelids in the image of the eye, the subimage $I_1$ satisfying $I_1=I_1(x', y')$, for $0 \le x' \le x_1$ and $y_1/4 \le y' \le 3y_1/4$; and step 304, acquiring all positive integers INT (y') satisfying $y_1/4 \le y' \le 3y_1/4$, determining a maximum value of x' and a minimum value of x' corresponding to each of the positive integers INT (y'), subtracting the minimum value of x' from the maximum value of x' to obtain a maximum difference value of x' corresponding to each of the positive integers INT (y'), and taking a maximum value in the maximum difference values of x' corresponding to all of the positive integers INT (y') as the max horizontal radius $L_p$ being expressed as:

$$L_p = \max_{i=1}^{n}[x_{max}(\mathrm{INT}_i(y')) - x_{min}(\mathrm{INT}_i(y'))],$$

wherein $x_{max}(\mathrm{INT}_i(y'))$ and $x_{min}(\mathrm{INT}_i(y'))$ are respectively the maximum value of x' and the minimum value of x' corresponding to the i-th positive integer INT (y'); n is the number of the positive integers INT (y') satisfying $y_1/4 \le y' \le 3y_1/4$, and $1 \le i \le n$.

The method for determining the proportionality factor η in the step 40 is as follows:

$$\eta = \frac{L_r}{L_p},$$

wherein $L_r$ is an actually measured value of a max horizontal radius of any dark part of an eye of the person.

Said step 50 comprises: performing 3D modeling by the mobile device or the computer based on the four basic data of the spectacle frame, and transmitting the results of the 3D modeling to the data center or the 3D printer to obtain a customized spectacle frame.

Said step 50 comprises: establishing a spectacle frame model by the mobile device or the computer based on the four basic data of the spectacle frame in combination with appearance parameters of the spectacle frame; matching the spectacle frame model with the front-view image and the side-view image respectively, or matching the spectacle frame model with the frame of front-view image and the frame of side-view image respectively; causing the spectacle frame model to be worn in the front-view image and the side-view image, and generating a virtual reality spectacle frame on a moving head via an image conversion tool, and obtain a customized spectacle frame based on the virtual reality spectacle frame.

The appearance parameters of the spectacle frame include colors and styles of the spectacle frame.

Compared with the prior art, the present invention has the following beneficial effects.

(1) The max horizontal radius of the dark part of an eye is measured, so as to obtain the proportionality factor of the actual size to the image size, and thus the off-site measurement of distance between any two points on the human body is achieved. The method provides accurate data and can be extensively applied.

(2) The parameters of a spectacle frame are collected through measurements on the front-view image and the side-view image, guaranteeing true and accurate data and providing a comfortable spectacle frames.

(3) People can perform a 3D modeling based on the actual pupil distance $L_1'$, the actual width $L_2'$ of the nose bridge, the actual distance $L_3'$ from the cornea apex to the top of the ear and the actual height H' of the nose bridge on a mobile device or a computer, and fabricate a spectacle frame with a 3D printer; they can also transmit the data to a data center, and an eyeglass store or an optometry center connected to the data center will design the spectacle frame. In this way, a lot of time is saved.

DETAILED DESCRIPTION

The present invention will be further described in detail in conjunction with the drawings and specific embodiments.

Embodiment 1

Figure 1:
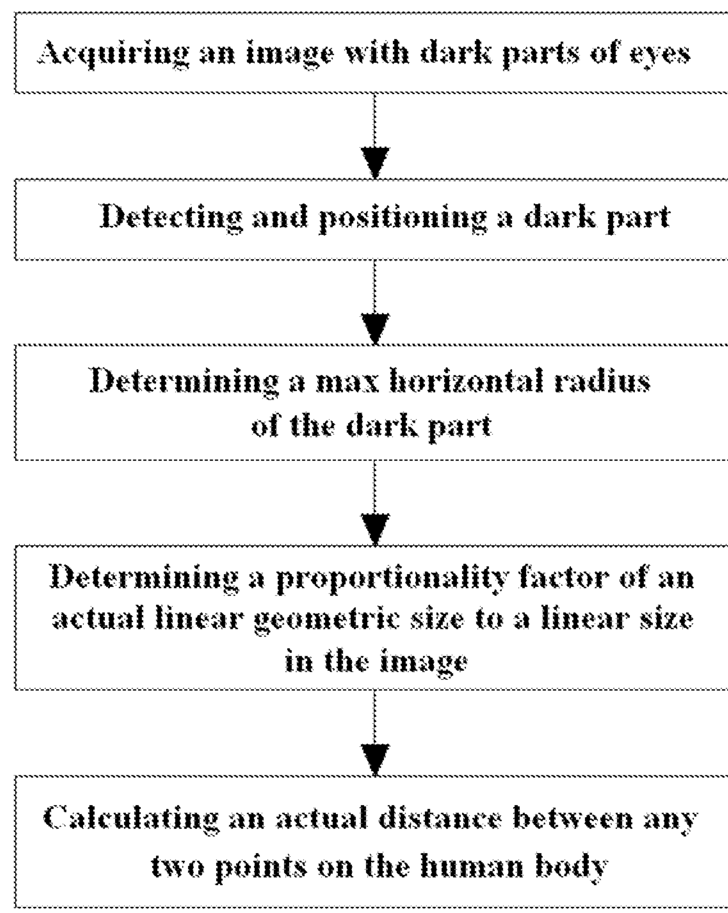
FIG. 1 is a flow chart of a method of the present invention for measuring an actual distance of a human body based on an image of cornea.

Provided is a method for measuring an actual distance of a human body based on an image of cornea, which enables measuring the body parameters off-site. As shown in FIG. 1, the method comprises the following steps.

Step 1, acquiring a photograph with one or both dark parts of eyes in it, or capturing a frame of image with one or both dark parts of eyes in it from a video.

In step 1, the angle for shooting the image or the video is not limited, and the only requirement is that one or both dark parts of eyes are included in the photograph or the frame (herein the image of the dark part can be approximately considered as an image of cornea). It should be noticed that, in the instant application, photographs or frames those have only one dark part suffice; however, if there are two dark parts in the photo or frame, then select the larger one, and the selecting is conducted by the computer or mobile device, In a preferred embodiment, the photograph or the frame captured from the video is preferred to be a front-view image, where the two dark parts are identical in diameter. Meanwhile, since a video consists of a plurality of frames of images (at least 100 images in a 5-second video), which comprise images of the human body in different angles including the front-view images, and as such, in another preferred embodiment, the images of human body are collected in the way of video.

Step 2, detecting and positioning the dark parts in the photograph or the frame of image.

This step may be manually performed, or automatically performed with a computer. At present, there are a few mature methods and software for automatically detecting and positioning eyes (specifically, the dark part of the eyes) on a human face in an image (specifically referring to a photograph or an image in a video) with a computer, such as those disclosed in the following references.

1, David Balya, Tamas Roska, Face and Eye Detection by CNN Algorithms, Journal of VLSI Signal Processing 23, (1999), pp. 497-511.

2, Antonio Haro, Myron Flickner, Irfan Essa, Detecting and tracking eyes by using their physiological properties, dynamics, and appearance, Proc. of IEEE International Conference on Computer Vision and Pattern Recognition, 2000, Vol. 1, pp. 163-168.

3, So-Hee Park, Jang-Hee Yoo, A new implementation method of ASEF for eye detection, 2012 7th International Conference on Computing and Convergence Technology (ICCCT), pp. 1034-1037.

4, Eye detection and tracking using opencv.\http://opencv-code.com/tutorials/eye-detection-and-tracking/.

The above references have mentioned related techniques, and thus it is not necessary to illustrate in detail herein.

Step 3, determining a max horizontal radius $L_p$ of one dark part in the photograph or the frame of image.

In this steps, the dark parts of eyes are introduced, for the following reasons. Firstly, an eye (especially that of the Chinese people) mostly consists of a white part and a dark part, and the obvious dividing line between these two parts facilitates collecting data of the dark part; moreover, there is little interference from the white part. Second, though sizes of eyes vary for different person, there is generally no difference in the actual max horizontal radius of the dark part of an eye after age 3 of a normal person when the growth of eyeballs is basically complete, which facilities the determination of proportionality factor in step 4.

This step approximately comprises:

step 31, placing the front-view image in a first quadrant of an X-Y coordinate system;

step 32, selecting a image I of one of the eyes in the front-view image, and obtaining a set I (x,y) of positive integers x and y in the image I of the eye, wherein $0 \le x \le x_1$, $0 \le y \le y_1$, and $x_1$ and $y_1$ are respectively a maximum horizontal coordinate and a maximum vertical coordinate in the front-view image;

step 33, capturing a subimage $I_1$ from the image I of eye for eliminating interferences of upper and lower eyelids in the image of the eye, the subimage $I_1$ satisfying $I_1 = I_1(x', y')$, for $0 \le x' \le x_1$ and $y_1/4 \le y' \le 3y_1/4$; and step 34, acquiring all positive integers INT (y') satisfying $y_1/4 \le y' \le 3y_1/4$, determining a maximum value of x' and a minimum value of x' corresponding to each of the positive integers INT (y'), subtracting the minimum value of x' from the maximum value of x' to obtain a maximum difference value of x' corresponding to each of the positive integers INT (y'), and taking a maximum value in the maximum difference values of x' corresponding to all of the positive integers INT (y') as the max horizontal radius $L_p$ being expressed as:

$$L_p = \max_{i=1}^{n}[x_{max}(\mathrm{INT}_i(y')) - x_{min}(\mathrm{INT}_i(y'))],$$

wherein $x_{max}(\mathrm{INT}_i(y'))$ and $x_{min}(\mathrm{INT}_i(y'))$ are respectively the maximum value of x' and the minimum value of x' corresponding to the i-th positive integer INT (y'); n is the number of the positive integers INT (y') satisfying $y_1/4 \le y' \le 3y_1/4$, and $1 \le i \le n$.

Step 4, determining a proportionality factor η of an actual linear geometric size to a linear size in the photograph or the frame based on the max horizontal radius $L_p$.

The method for determining the proportionality factor η is as follows:

$$\eta = \frac{L_r}{L_p},$$

wherein $L_r$ is the actually measured value of the transverse maximum length of the dark part of eye on human body corresponding to that in the photographed or the frame of image. The actual value of the max horizontal radius of cornea can be considered as a constant value; the constant value varies slightly for different genders or races (such as the Yellow race and the Caucasian race), but is identical for people in the same population (referring to those of the same gender and race).

Step 5, measuring an actual image distance between any two points in the photograph or the frame of image, and multiplying the actual image distance by the proportionality factor η to obtain an actual distance between the two corresponding points on human body.

There are various methods for measuring an actual image distance between any two points in the photograph or the frame of image. In one embodiment, the steps are as follows: after performing positioning based on a standard image (obtained by measuring in the same distance) for the front-view photograph and the side-view photograph which are taken the person who wishes to obtain the spectacles of himself/herself, then establishing a right-angled triangle in an X-Y coordinate system (preferably, in a first quadrant) with the coordinates of the two points, and performing the measuring. Let the coordinates of the two points in the first quadrant of the X-Y coordinate system are respectively ($x_a$, $y_a$) and ($x_b$, $y_b$), then the distance between the two points in the photograph or the frame of image is as $\sqrt{(x_a-x_b)^2+(y_a-y_b)^2}$, and as such the actual distance between the two points is as $\eta\sqrt{(x_a-x_b)^2+(y_a-y_b)^2}$, which can also be automatically calculated by the computer based on the coordinates of the two points.

Embodiment 2

Based on the above-mentioned principle, the present invention is further explained and described by taking customizing a spectacle frame as an example.

Figure 2:
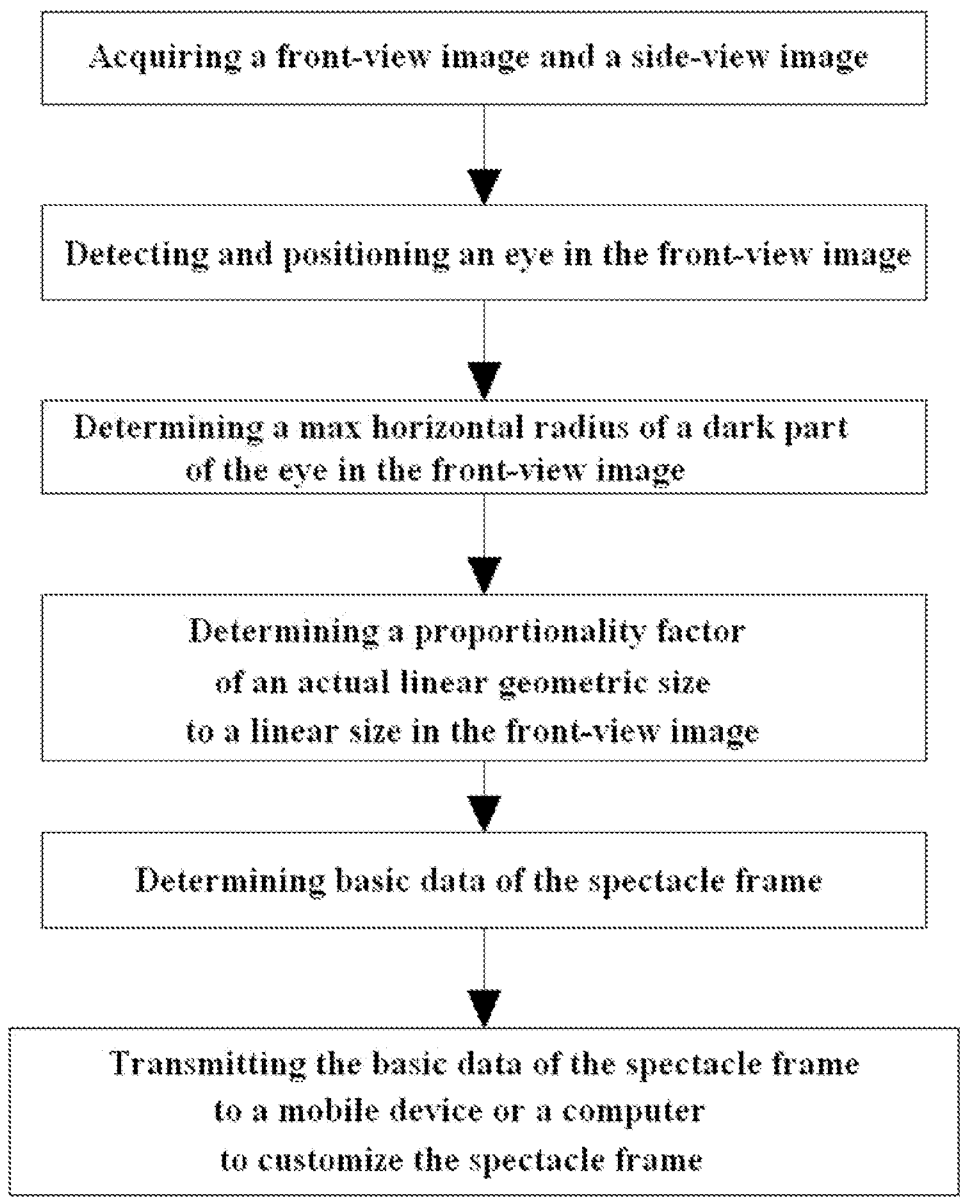
FIG. 2 is a flow chart of a method of the present invention for customizing a spectacle frame.

As shown in FIG. 2, a method for customizing a spectacle frame comprises the following step'.

Step 10, taking photographs of a human face of a person by a mobile device or a computer to obtain a front-view image and a side-view image from the photographs; or capturing two frames of images with front view and side view of a human face from a video with the human face.

The frame of front-view image and the front-view photograph are treated in the same way. The following description is directed to the front-view image, but the side-view image can also be treated in the same way.

The distance from the mobile device to the person is preferably 33 cm (1 Chinese foot). On one hand, this is the conventional distance for prescribing spectacles, which facilitates designing and fabricating the spectacle frame; on the other hand, uniform sizes are applied in the front-view image and the side-view image, which facilitate subsequent measurement. The mobile device is a handheld device, preferably a mobile phone or a tablet computer, in which related clients can be installed, facilitating subsequent 3D modeling.

Step 20, detecting and positioning one eye in the front-view image. See step 2 of the embodiment 1 for reference.

Step 30, determining a max horizontal radius $L_p$ of a dark part of the eye in the front-view image. See step 3 of the embodiment 1 for reference.

Step 40, determining a proportionality factor $\eta$ of an actual linear geometric size to a linear size in the front-view image based on the max horizontal radius $L_p$. See step 4 of the embodiment 1 for reference.

Step 50, based on a pupil distance $L_1$, a width $L_2$ of a nose bridge in the front-view image, measuring a distance $L_3$ from a cornea apex to a top of an ear and a height H of the nose bridge (a vertical distance from the midpoint of a profile of the nose bridge to a face plane) in the side-view image, and multiplying the pupil distance $L_1$, the width $L_2$ of the nose bridge, the distance $L_3$ from the cornea apex to the top of the ear and the height H of the nose bridge respectively by the proportionality factor $\eta$ to obtain an actual pupil distance $L_1'$, an actual width $L_2'$ of the nose bridge, an actual distance $L_3'$ from the cornea apex to the top of the ear and an actual height H' of the nose bridge of the person.

The method for measuring the pupil distance $L_1$, the width $L_2$ of a nose bridge and the height H of the nose bridge in the front-view image, and the distance $L_3$ from a cornea apex to a top of an ear in the side-view image, is identical with the method in step 5 of embodiment 1 for measuring an actual image distance between any two points in the photograph or the frame of image. In order to improve the accuracy, one can further measure a protruding height of the nasal root, and a degree of an included angle between two edges of the nose bridge within 2 cm from the nasal root.

Step 60, making an spectacle frame to order via 3D modeling: transmitting the actual pupil distance $L_1'$, the actual width $L_2'$ of the nose bridge, the actual distance $L_3'$ from the cornea apex to the top of the ear and the actual height H' of the nose bridge of the person to the mobile device or the computer to perform a 3D modeling.

The method for modeling is simple. Diameter data of the spectacle frame can be obtained based on the actual pupil distance $L_1'$, bridge length and nosepad width data of the spectacle frame can be obtained based on the actual width $L_2'$ of the nose bridge, leg length data of the spectacle frame can be obtained based on the actual distance $L_3'$ from the cornea apex to the top of the ear, bending of the nosepad can be obtained based on the actual height H' of the nose bridge, and a 3D modeling can be establishing based on the above data. Results of the 3D modeling are then transmitted, together with conventional data (such as the shapes, the materials, the patterns and the colors of the frame and the legs), to a data center or a 3D printer. People can design and fabricate spectacle frames by themselves by transmitting the data to the 3D printer. However, if it is not possible to do it themselves, they can also transmit the data to a data center, and an eyeglass store or an optometry center connected to the data center will design and fabricate the spectacle frame, which saves a lot of time.

Step 60', establishing the model through a virtual reality method: generating a virtual reality spectacle frame tracing the movement of a human face (head). Compared with the method of directly fabricating the spectacle frame via a 3D printer in the step 60, the virtual reality method introduces appearance parameters of the spectacle frame and thereby has better pertinence; moreover, through tracing and compensating for the movement of the head, the perspective effect of virtual reality is improved, such that the visual system and the motion-sensing system of the user is linked, and therefore the user experience is enhanced (the user can see the virtual wearing effect of spectacles in a mobile device), people can fabricating spectacle frame fitting themselves better.

The principle thereof is as follows. First, the actual pupil distance $L_1'$, the actual width $L_2'$ of the nose bridge, the actual distance $L_3'$ from the cornea apex to the top of the ear and the actual height H' of the nose bridge are transmitted to a mobile device or a computer, and combined with the appearance parameters such as colors and styles (stored in a database and selected from the database respectively) to establish a model of the spectacle frame. Then the model is caused to be worn to the eyes in the front-view image in a proper angle, and a three-dimension model of a human head wearing the model of the spectacle frame is established with an image conversion tool (such as 3DMAX® and CURA®). The effect of wearing the spectacle frame is illustrated by the movement of the three-dimension model of the human head. When the spectacle frame model meets the requirements of the user, the desired spectacle frame is fabricated by 3D printing. In order to establish a human head model much more clear and smooth and avoid distortions, more images (such as side-view image) can be introduced to combine with the spectacle frame model in the image conversion tool.

Although the present invention has been described by the specific embodiments, it will be apparent to those skilled in the art that various changes and equivalent substitutions may be made to the present invention without departing from the scope of the present invention. In addition, various modifications may be made to the present invention without departing from the scope of the invention for a particular situation or application. Accordingly, the present invention is not limited to the specific embodiments disclosed, but should cover all embodiments falling within the scope of the present invention.

The invention claimed is:

1. A method for measuring an actual distance of human body based on an image of cornea, comprising the following steps:

step 1, acquiring a front-view photograph with at least one dark part of eyes, or capturing a frame of a front-view image with the at least one dark part of eyes from a video;

step 2, detecting and positioning a first dark part in the front-view photograph or the frame of the front-view image;

step 3, determining a max horizontal radius $L_p$ of the first dark part;

step 4, determining a proportionality factor η of an actual linear geometric size to a linear size in the photograph or the frame base on the max horizontal radius $L_p$; and step 5, measuring an actual image distance between any two points in the front-view photograph or the frame of front-view image, and multiplying the actual image distance by the proportionality factor η to obtain an actual distance between the two corresponding points on human body.

2. The method for measuring an actual distance of human body based on an image of cornea according to claim 1, wherein the step 3 comprises the following sub-steps:

step 31, placing the first dark part in a first quadrant of an X-Y coordinate system;

step 32, selecting the first dark part, and obtaining a set I (x,y) of positive integers x and y in an image I of the first dark part, wherein $0 \le x \le x_1$, $0 \le y \le y_1$, and $x_1$ and $y_1$ are respectively a maximum horizontal coordinate and a maximum vertical coordinate in the image of the first dark part;

step 33, capturing a subimage $I_1$ from image I of the first dark part for eliminating interferences of upper and lower eyelids in the image of the first dark part, wherein the subimage $I_1$ satisfies $I_1 = I_1(x', y')$, wherein $0 \le x' \le x_1$ and $y_1/4 \le y' \le 3y_1/4$; and step 34, acquiring all positive integers INT (y') satisfying $y_1/4 \le y' \le 3y_1/4$, determining a maximum value of x' and a minimum value of x' corresponding to each of the positive integers INT (y'), subtracting the minimum value of x' from the maximum value of x' to obtain a maximum difference value of x' corresponding to each of the positive integers INT (y'), and taking a maximum value in the maximum difference values of x' corresponding to all of the positive integers INT (y') as the max horizontal radius $L_p$:

$$L_p = \max_{i=1}^{n}[x_{max}(\mathrm{INT}_i(y')) - x_{min}(\mathrm{INT}_i(y'))],$$

wherein $x_{max}(\mathrm{INT}_i(y'))$ and $x_{min}(\mathrm{INT}_i(y'))$ are respectively the maximum value of x' and the minimum value of x' corresponding to the i-th positive integer INT(y'); wherein n is the number of the positive integers INT (y') satisfying $y_1/4 \le y' \le 3y_1/4$, and $1 \le i \le n$.

3. The method for measuring an actual distance of human body based on an image of cornea according to claim 2, wherein the proportionality factor η in step 4 is determined as:

$$\eta = \frac{L_r}{L_p},$$

wherein, $L_r$ is an actually measured value of a max horizontal radius of an actual dark part of eye on human body corresponding to the first dark part.

4. A method for customizing a spectacle frame, comprising the following steps:

step 10, taking a plurality of photographs or a video of a human face of a person by a mobile device or a computer; acquiring a front-view image and a side-view image from the plurality of photographs, or acquiring a first frame of the front-view image and a second frame of the side-view image from the video;

step 20, detecting and positioning an eye in the front-view image;

step 30, determining a max horizontal radius $L_p$ of a dark part of the eye in the front-view image;

step 40, determining a proportionality factor η of an actual linear geometric size to a linear size in the front-view image base on the max horizontal radius $L_p$;

step 50, measuring a pupil distance $L_1$, a width $L_2$ of a nose bridge and a height H of the nose bridge in the front-view image, measuring a distance $L_3$ from a cornea apex to a top of an ear in the side-view image, and multiplying the pupil distance $L_1$, the width $L_2$ of the nose bridge, the distance $L_3$ from the cornea apex to the top of the ear and the height H of the nose bridge respectively by the proportionality factor η to obtain four basic data of the spectacle frame including an actual pupil distance $L_1'$, an actual width $L_2'$ of the nose bridge, an actual distance $L_3'$ from the cornea apex to the top of the ear and an actual height H of the nose bridge of the person; and step 60, transmitting the actual pupil distance $L_1'$, the actual width $L_2'$ of the nose bridge, the actual distance $L_3'$ from the cornea apex to the top of the ear and the actual height H' of the nose bridge of the person to the mobile device or the computer to customize the spectacle frame.

5. The method for customizing a spectacle frame according to claim 4, wherein the step 30 comprises the following sub-steps:

step 301, placing the front-view image in a first quadrant of an X-Y coordinate system;

step 302, selecting an image I of the eye in the front-view image, and obtaining a set I (x,y) of positive integers x and y in image I of the eye, wherein $0 \le x \le x_1$, $0 \le y \le y_1$, and $x_1$ and $y_1$ are respectively a maximum horizontal coordinate and a maximum vertical coordinate in the front-view image;

step 303, capturing a subimage $I_1$ from image I of eye for eliminating interferences of upper and lower eyelids in the image of the eye, wherein the subimage $I_1$ satisfies $I_1 = I_1(X', y')$, wherein $0 \le x' \le x_1$ and $y_1/4 \le y' \le 3y_1/4$; and step 304, acquiring all positive integers INT (y') satisfying $y_1/4 \le y' \le 3y_1/4$, determining a maximum value of x' and a minimum value of x' corresponding to each of the positive integers INT (y'), subtracting the minimum value of x' from the maximum value of x' to obtain a maximum difference value of x' corresponding to each of the positive integers INT (y'), and taking a maximum value in the maximum difference values of x' corresponding to all of the positive integers INT (y') as the max horizontal radius $L_p$:

$$L_p = \max_{i=1}^{n} [x_{max}(\mathrm{INT}_i(y')) - x_{min}(\mathrm{INT}_i(y'))],$$

wherein $x_{max}(\mathrm{INT}_i(y'))$ and $x_{min}(\mathrm{INT}_i(y'))$ are respectively the maximum value of x' and the minimum value of x' corresponding to the i-th positive integer INT (y'); wherein n is the number of the positive integers INT (y') satisfying $y_1/4 \leq y' \leq 3y_1/4$, and $1 \leq i \leq n$.

6. The method for customizing a spectacle frame according to claim 4, wherein the proportionality factor η in step 40 is determined as:

$$\eta = \frac{L_r}{L_p},$$

wherein $L_r$ is an actually measured value of a max horizontal radius of any dark part of an eye of the person.

7. The method for customizing a spectacle frame according to claim 4, wherein the step 50 comprises the sub-steps of:

performing 3D modeling by the mobile device or the computer based on the four basic data of the spectacle frame, and transmitting a result of the 3D modeling to a data center or the 3D printer to obtain the customized spectacle frame.

8. The method for customizing a spectacle frame according to claim 4, wherein the step 50 comprises the sub-steps of:

establishing a spectacle frame model by the mobile device or the computer base on the four basic data of the spectacle frame in combination with a plurality of appearance parameters of the spectacle frame;

matching the spectacle frame model with the front-view image and the side-view image respectively, or matching the spectacle frame model with the first frame of the front-view image and the second frame of the side-view image respectively;

wearing the spectacle frame model on the front-view image and the side-view image respectively, and generating a virtual reality spectacle frame on a moving head via an image conversion tool, to obtain a customized spectacle frame based on the virtual reality spectacle frame.

9. The method for customizing a spectacle frame according to claim 8, wherein the plurality of appearance parameters of the spectacle frame include a color and a style of the spectacle frame.

* * * * *